United States Patent [19]

Frenkel et al.

[11] Patent Number: 5,045,313

[45] Date of Patent: Sep. 3, 1991

[54] VACCINE FOR IMMUNIZING CATS AGAINST TOXOPLASMA OOCYST SHEDDING

[75] Inventors: Jacob K. Frenkel, Overland Park, Kans.; Elmer R. Pfefferkorn, Hanover, N.H.

[73] Assignees: The University of Kansas, Lawrence, Kans.; Darmouth College, Hanover, N.H.

[21] Appl. No.: 376,809

[22] Filed: Jul. 7, 1989

[51] Int. Cl.$^5$ ...................... A61K 39/00; C12N 15/00
[52] U.S. Cl. ......................... 424/88; 424/93; 435/172.1; 435/243; 435/258
[58] Field of Search ................. 424/88, 93; 435/172.1, 435/243, 258

[56] References Cited

U.S. PATENT DOCUMENTS 4,473,548  9/1984  Frenkel et al. ..................... 424/88

OTHER PUBLICATIONS

Freukel et al., Journal Parasitology, vol. 68, No. 5, pp. 744–748, 1982.
E. R. Pfefferkorn and Lorraine C. Pfefferkorn, Toxoplasma gondii: Isolation and Preliminary Characterization of Temperature-Sensitive Mutants, Sept. 8, 1975.
J. K. Frenkel and S. A. Caldwell, Specific Immunity and Nonspecific Resistance to Infection: Listeria, Protozoa, and Viruses in Mice and Hamsters, 3/75.
J. K. Frenkel, MD, PhD, Common Questions on Toxoplasmosis: Veterinary, Medical, and Public Health Considerations, Aug. 1982.
J. K. Frenkel, M.D., PhD, Toxoplasmosis in Cats and Man, Jan.–Feb., 1975.
Marjorie L. Melton and Harley G. Sheffield, Activity of the Anticoccidial Compound, Lasalocid, Against Toxoplasma Gondii in Cultured Cells, 1/17/75.
Harley G. Sheffield and Marjorie L. Melton, Effects of Pyrimethamine and Sulfadiazine on the Intestinal Development of Toxoplasma Gondii in Cats, Oct. 1975.
J. P. Dubey and R. A. Yeary, Anticoccidial Activity of 2-Sulfamoyl-4,4-Diaminodiphenylsulfone, Sulfadiazine, Pyrimethamine and Clindamycin in Cats Infected with Toxoplasma Gondii, Mar. 1977.
Joseph D. Schwartzman and E. R. Pfefferkorn, Pyrimidine Synthesis by Intracellular Toxoplasma Gondii, Jul. 31, 1980.
E. R. Pfefferkorn and Lorraine C. Pfefferkorn, Quantitative Studies of the Mutagenesis of Toxoplasma Gondii, Aug. 1978.
J. K. Frenkel and Donald D. Smith, Immunization of Cats Against Shedding of Toxoplasma Oocysts, 1/7/82.
Jacob K. Frenkel, Toxoplasmosis, 1984.
H. Waldeland, E. R. Pfefferkorn, and J. K. Frenkel, Temperature-Sensitive Mutants of Toxoplasma Gondii: Pathogenicity and Persistence in Mice, Jul. 21, 1982.
H. Waldeland, and J. K. Frenkel, Live and Killed Vaccines Against Toxoplasmosis in Mice, Jul. 21, 1982.
J. K. Frenkel and D. D. Smith, Inhibitory Effects of Monensin on Shedding of Toxoplasma Oocysts by Cats, Feb. 17, 1982.

*Primary Examiner*—Margaret Moskowitz
*Assistant Examiner*—Abdel A. Mohamed
*Attorney, Agent, or Firm*—Hovey, Williams, Timmons & Collins

[57] ABSTRACT

A new mutant strain vaccine, and a corresponding method of immunization, against Toxoplasma in cats is provided which makes use of a reproductively deficient strain of *T.gondii*, designated T-263. Bradyzoites in tissue cysts from laboratory animals infected with the mutant were fed to cats, which developed immunity against subsequent *T.gondii* challenge without concomitant shedding of infectious oocysts. The new vaccine eliminates the need for chemoprophylaxis subsequent to primary infection.

3 Claims, No Drawings

VACCINE FOR IMMUNIZING CATS AGAINST TOXOPLASMA OOCYST SHEDDING

The United States Government has rights in this invention pursuant to Grant Nos. Al14151-12 and Al07489-20 awarded by the Public Health Service of the U.S. Department of Health and Human Services.

BACKGROUND OF THE INVENTION

1. Field of the Invention

The present invention is broadly concerned with a method of immunizing cats against Toxoplasmosis wherein use is made of a live, reproductively deficient mutant of *Toxoplasma gondii*. More particularly, it is concerned with such a method, and the associated vaccine, wherein the mutant is designated T-263 and has ATCC Accession No. 40615.

2. Description of the Prior Art

Toxoplasmosis is a parasitic disease, and research has indicated that the parasite has a complicated life cycle with the infection spreading to many animals. Oocysts (egg spores) are shed in the feces of domestic cats and certain types of wild cats. Oocysts are then spread by contact with the feces. Flies and cockroaches, which eat feces, can serve as transport agents, contaminating animals which do not directly encounter the cat feces. Mice and birds can be infected either from transport agents, or through direct contact and can then spread the infection to animals which prey on them. Humans can be infected by eating raw or rare meats, or by direct contact with infected cat feces, or contaminated soil.

Toxoplasma infections are quite prevalent, with one-quarter to one-half of the adults in the United States and elsewhere asymptomatically infected. While the presence of Toxoplasma infections has long been known, little was discovered about the transmission of Toxoplasma until the late 1930's and 1940's when Toxoplasmosis was found in newborn babies in the U.S. However, the life cycle of Toxoplasma, and the central role played therein by cats, has now been conclusively established.

The spectrum of human disease due to Toxoplasmosis was characterized by a combination of serologic, immunologic and epidemiological studies, and by isolation of the causative agent, *Toxoplasma gondii*. In the acute infection where cells are destroyed by rapidly proliferating organisms, there may occur fever, pneumonia, and inflammation of the heart muscle, liver and skin (rash). Toward the end of the period or following a subclinical acute infection, localized or generalized swelling of lymph nodes is observed, especially in women. In newborns infected in utero, a subacute disease picture is typical. In addition to the symptoms of acute Toxoplasmosis mentioned above, meningoencephalitis ("brain fever"), often with hydrocephalus ("water on the brain"), and retinochoroiditis (intraocular inflammation) are important. Most of the mothers who have given birth to infected babies had infections without symptoms.

Thus, Toxoplasmosis deserves special attention because of the serious danger it raises for the unborn human baby. A pregnant woman may have the infection and unknowingly infect the fetus. If not diagnosed and treated in time, her child may be born with permanent brain and eye damage. For this reason, efforts to prevent infection during pregnancy are important.

Inasmuch as domestic cats are important spreaders of Toxoplasma oocysts which are shed in their feces, attempts have been made in the past to immunize domestic cats against oocyst shedding. Generally speaking, prior successful immunizations have required primary infection of cats with Toxoplasmosis, followed by the usual oocyst shedding and a buildup of immunity. However, this manner of immunization generates the very phenomenon sought to be avoided, i.e., oocyst shedding, and as such is deemed deficient. This is especially the case when it is considered that infectious oocysts tend to remain active for a period of months up to a year and a half. Meanwhile, attempts to immunize cats using bradyzoites of oocystless Toxoplasma strains have proven unsuccessful.

A successful approach to immunization of cats is described in U.S. Pat. No. 4,473,548, which involves chemoprophylactic treatment of cats after primary Toxoplasma infection, so as to suppress oocyst shedding while giving immunity. In this procedure, cats are initially infected and thereafter monensin or salinomycin is orally administered for essentially preventing oocyst shedding while permitting immunization to develop in the cats. Although monensin was well accepted by kittens without apparent toxicity, hesitancy existed in using monensin because of occasional toxicity problems which have been described in other animals. Furthermore, human tolerance for monensin has not been investigated, and this constitutes another reason for the lack of acceptance of monensin prophylaxis.

Accordingly, there is a decided need in the art for a method of immunizing cats against Toxoplasmosis which eliminates the problem of fecal oocyst shedding while avoiding use of prophylactic drug treatment.

SUMMARY OF THE INVENTION

The present invention overcomes the problems described above and provides a method (and a corresponding vaccine) for the immunization of cats against *T.gondii* challenge which eliminates the phenomenon of oocyst shedding in the vaccinated cats.

Broadly speaking, the method of the invention involves administering to cats (preferably orally) an effective amount of a vaccine comprising a specific mutant of *T.gondii* which has been found to immunize 84% of cats without the need of chemoprophylaxis. This level of immunization is very similar to that found using the method described in U.S. Pat. No. 4,473,548 (85%).

The specific mutant useful in the invention has been designated T-263, and has been deposited with the American Type Culture Collection, 12301 Parklawn Drive, Rockville, Maryland 20852, USA, on July 25, 1989. The mutant has been accorded ATCC Accession No. 40615. The mutant was one of a large number produced by exposing tachyzoites of Toxoplasma of the known "C" strain to an alkylating agent, N-methyl-N'-nitro-N-nitrosoguanidine (Pfefferkorn, E. R., and Pfefferkorn, L. C. Toxoplamas gondii: Isolation and preliminary characterization of temperature-sensitive mutants. Experimental Parasitology 39, 365–376, 1976.) In plaque assays, mutagenized tachyzoites were selected for their resistance to adenine arabinoside, and one clone was selected for resistance to 5-fluoro-deoxyuridine. The adenine arabinoside-resistant mutants, were again mutagenized with the same mutagen or with ethyl nitrosourea, and selected clones were tested for suitability as a vaccine. A total of 117 mutants were tested as vaccines in cats, and of this number only a single mutant, T-263, met the dictates of the invention.

DESCRIPTION OF THE PREFERRED EMBODIMENT

The following is a description of the mutagenesis, screening and testing of the T-263 Toxoplasma mutant useful in the invention. Literature references cited herein are incorporated by reference.

A. Materials and Methods

Mice utilized in the experiments were CF-1 mice obtained from SASCO, Inc. (Omaha, NE). Young kittens were mostly obtained from random source pregnant cats. These had been donated or were on loan to the Animal Care Unit at the University of Kansas Medical Center in response to newspaper advertisements requesting pregnant cats or kittens for research. In addition, laboratory reared kittens from Theracon, Inc. Topeka, KS were used. All kittens were serologically tested for Toxoplasma antibody, and examined for fecal parasites prior to use. All kittens used were seronegative; *Toxocara* eggs and *Cystoisospora felis* and *C. rivolta* oocysts were found occasionally, but no Toxoplasma oocysts were found. The kittens obtained from Theracon showed *C. rivolta* oocysts only.

Toxoplasma was grown in a cell culture system composed of human skin fibroblasts. After exponential growth was reached and at a stage when 8 organisms were present per cell, a mutagen, ethylnitrosourea was added. The ethyl-nitroso-urea concentration was 300 micrograms per milliliter and the duration of treatment was for four hours. Survival was measured at this point and the survival rate was 3% compared to control cultures. At the end of the mutagen exposure the medium was removed and the organisms were grown for another two days in culture, being subcultured every day. At this point dilutions of Toxoplasma were seeded into 96 well trays, and 117 clones were further analyzed.

Clones of Ara-A resistant Toxoplasma were grown in human fibroblast tissue cultures for short periods of time, but were normally maintained as chronic infections in mice. These were injected either subcutaneously (sc) or intraperitoneally (ip) and to prevent illness and permit development of bradyzoites in tissue cysts, the mice were treated from days 3 to 14 with sulfamerazine-sodium (Sigma Chemical Co., St. Louis, MO) 15 mg/100 ml of water, given ad libitum to drink. After at least one month, a mouse infected with a particular strain was killed, bled to be checked for the development of antibody, and a brain smear examined by light microscopy for the presence of cysts of Toxoplasma. The carcass of a mouse infected with a given candidate strain was then fed to one or several seronegative, weaned kittens and the feces were examined for the presence of oocysts over the next 30 days.

Feces were usually collected daily for examination from 5 days through 12, and then usually three times weekly for up to 30 days. Oocysts were concentrated by flotation in a sucrose solution of specific gravity of 1.15 and stored in 2% (v/v) sulfuric acid to permit sporulation. Intensity of shedding was graded on a scale of 1 to 4, with 1+ indicating only one oocyst found on a slide, 2+ being several to numerous oocysts on a slide, +3 being an average of one oocyst per high power field, and +4 being numerous oocysts per high power (=400x) field. In some experiments, oocysts were counted in a hemacytometer using standard techniques.

When a cat was found not to shed oocysts after primary infection with a candidate mutant, it was challenged (po) with an inoculum of T-265 bradyzoites, and again checked for oocyst production over a period of 30 days. When visual examination failed to identify oocysts after exposure, the apparent failure of shedding was verified by the inoculation of the combined sucrose float supernatants of the 5 to 12 day specimens into mice. The samples were neutralized with 3.3% (W/V) sodium hydroxide, using phenol red as an indicator, spun down, and the sediment was fed or injected (ip) into groups of several mice.

When mice died, impression smears were made of lung, liver, spleen and brain, stained with Giemsa, and examined for the presence of Toxoplasma. Survivors were bled after 21 days and tested serologically for the presence of antibody for Toxoplasma.

Cats were bled from the ear before exposure to tissues of infected mice, at least 30 days thereafter, and following challenge infection. Mice were bled from the retroorbital sinus while under ether anesthesia. Antibody titers were determined by ther Sabin-Feldman dye test (Frenkel and Jacobs, "Ocular Toxoplasmosis", *A.M.A. Arch. Ophth.* 1958), using tachyzoites of the RH strain of Toxoplasma, maintained as acute infections in mice and passed thrice weekly (ip).

After a candidate mutant strain had failed to produce oocysts in 3 cats after primary exposure, and had immunized these 3 cats, an attempt was made to detect whether that strain was capable of forming gametes. Mouse tissues containing bradyzoites of the Ara-A resistant (non-oocyst forming) vaccine candidate strain were mixed with tissues containing bradyzoites of a FUDR resistant oocyst-producing strain; the mixture was fed to one or several kittens. Production of oocysts incorporating both Ara-A and FUDR resistance indicated recombination of the two genomes, because of production of one gamete by the candidate strain (Pfefferkorn, L. C., and Pfefferkorn, E. R. Toxoplasma gondii: Genetic recombination between drug resistant mutants. Experimental Parasitology 50, 305–316, 1980.)

Presence of cysts of Toxoplasma in brain of mice was determined microscopically; one or several brains were fed to kittens; infection was evaluated by oocyst shedding, and in its absence, by seroconversion. Oocyst numbers were estimated visually, and quantitated by titration in 6 mice and after exposure to excystation fluid in fibroblast cultures. The number of mice with Toxoplasma in smears and of the seropositive animals were combined to determine the $ID_{50}$. In cell cultures the presence of plaques in certain dilutions served as indicator of infection.

B. RESULTS

A total of 117 mutagenized araA®mutants were tested in cats as described above. 106 mutants gave rise to oocyst shedding and were discarded. Of these, 85 mutants gave rise to oocysts shedding in the first cat, 16 in the second cat, 3 in the third. Two mutants were tested in 11 or 12 cats, with shedding observed in 6 of 11 and, 2 of 12.

The infection with 10 mutants was not accompanied by oocyst shedding. Of these, infections with 6 mutants did not confer immunity, and 3 mutants were lost. One mutant, denominated T-263, was tested in a total 37 cats, none of which shed oocysts, determined visually and by mouse inoculation. When these cats were challenged, 31 or 83.7% were immune. This includes a group of 5 kittens challenged after 6 months, of which 3 were immune. Results of these tests are set forth in the following Table:

| | Vaccination of Cats | | | | Results of Challenge with (Complete Strain) | | | | Protective Index |
|---|---|---|---|---|---|---|---|---|---|
| | Oocyst Shedding | | Reciprocal antibody titer | | Oocyst shedding | | Reciprocal antibody titer | | |
| | visually | mouse inoc. | Range | Geometric mean | visually | mouse innoc | Range | Geometric mean | |
| T-263 Vaccine | 0/37 | 0/37 | <2–128 | 9.2 | 6/37 | 6/37 | <2/128 | 6.9 | 84% |
| T-265 | — | — | — | — | 16/16 | 16/16 | 16–512 | 97 | |
| | | | | | P = <0.001 | | | | |

In order to test for presence of either male or female gametes by T-263, bradyzoites of this ara-A®mutant were fed to cats simultaneously with bradyzoites of T-237, an FUDR®oocyst producer. The resultant oocysts were cloned and tested for ara-A resistance. In three different experiments, 3%, 1.5%, and 0.01% of oocysts were found to be ara-A resistant, with 0.1%, 0.1%, and 0.01% of oocysts doubly resistant.

To assess the sensitivity of visually determining the number of oocysts, a suspension was counted and titrated. In the presence of a visual count of 50,000 oocysts, oral titration in mice yielded 10,000, subcutaneous titration 19, and titration in human skin fibroblast cultures 4,400 infectious units.

As described, the vaccine comprising the T-263 mutant immunized essentially 84% of the cats challenged. This is a slightly lower, but statistically insignificant, immunization protection than that afforded by infection with normal bradyzoites which gives concomitant oocyst shedding (88%–94%). (Frenkel, J. K., and Smith, D. D. Immunization of cats against shedding of Toxoplasma oocysts. Journal of Parasitology 68(5):744–748, 1982.) A particular advantage of the new vaccine and method is that it eliminates chemoprophylaxis with monensin or the like; at the same time, immunization in accordance with the invention does not lead to oocyst formation. The occurrence of the ara-A®gene and of genetic recombination, although in low incidence, suggests that the T-263 mutant forms one gamete, and according the mutant has been designated "reproductively deficient" to characterize this attribute.

The T-263 mutant to be used for vaccination purposes has been successfully propagated in mice in order to develop the uniquely infectious bradyzoites in cysts. Alternative methods would be the use of other small laboratory animals such as rats; or propagation in certain cell cultures, in which cyst formation occurs spontaneously or in the presence of antibody (Hoff et al. "Toxoplasma gondii Cysts in Cell Culture", J. Parasitol. 63:1121-24, 1977). In addition, while the bradyzoite cysts have been fed directly, if desired the vaccine may include a suitable carrier.

What is claimed is:

1. A method of immunizing cats against Toxoplasmosis without concomitant oocyst shedding by said cats, said method consisting essentially of administering to said cats an effective amount of a mutant of *T. gondii*, said mutant being designated as T-263 mutant and having ATCC Accession No. 40615.

2. The method of claim 1, said mutant being administered orally to said cats.

3. A vaccine for immunizing cats against Toxoplasmosis without concomitant oocyst shedding by said cats, said vaccine comprising a mutant of *T.gondii*, said mutant being designed as T263 and having ATCC Accession No. 40615.

* * * * *